US008969351B2

(12) United States Patent
Berghausen et al.

(10) Patent No.: US 8,969,351 B2
(45) Date of Patent: *Mar. 3, 2015

(54) CRYSTALLINE FORM OF AN INHIBITOR OF MDM2/4 AND P53 INTERACTION

(75) Inventors: Joerg Berghausen, Iorrach (DE); Haixia Ren, Shanghai (CN)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/298,351

(22) Filed: Nov. 17, 2011

(65) Prior Publication Data

US 2012/0129871 A1    May 24, 2012

(30) Foreign Application Priority Data

Nov. 19, 2010  (WO) ................ PCT/CN2010/078927

(51) Int. Cl.
*A61K 31/497* (2006.01)
*C07D 241/10* (2006.01)
*C07D 401/12* (2006.01)

(52) U.S. Cl.
CPC .................................. *C07D 401/12* (2013.01)
USPC ...................... 514/252.1; 544/336

(58) Field of Classification Search
CPC .................................................. C07D 401/12
USPC ..................... 514/253.05; 544/363
See application file for complete search history.

(56) References Cited

U.S. PATENT DOCUMENTS

| | | | |
|---|---|---|---|
| 3,829,420 A | 8/1974 | Inaba et al. | |
| 3,865,827 A | 2/1975 | Yamamoto et al. | |
| 3,923,710 A | 12/1975 | Ishizumi et al. | |
| 4,099,002 A | 7/1978 | Inaba et al. | |
| 4,258,187 A | 3/1981 | Middleton | |
| 4,335,127 A | 6/1982 | Vandenberk et al. | |
| 4,695,633 A | 9/1987 | Berneth et al. | |
| 2008/0153791 A1 | 6/2008 | Wilckens | |
| 2010/0160356 A1 | 6/2010 | Heinrich et al. | |
| 2011/0230457 A1* | 9/2011 | Berghausen et al. | 514/210.02 |

FOREIGN PATENT DOCUMENTS

| | | |
|---|---|---|
| EP | 1 657 238 A1 | 5/2006 |
| JP | 2001-302515 | 10/2001 |
| WO | WO 93/04047 A1 | 3/1993 |
| WO | 98/01467 A2 | 1/1998 |
| WO | WO 00/66560 A1 | 11/2000 |
| WO | WO 03/062392 A2 | 7/2003 |
| WO | WO 03/095625 A2 | 11/2003 |
| WO | WO 03/101985 A1 | 12/2003 |
| WO | WO 2004/096134 A2 | 11/2004 |
| WO | WO 2005/027882 A1 | 3/2005 |
| WO | WO 2006/024837 A1 | 3/2006 |
| WO | WO 2006/097337 A2 | 9/2006 |
| WO | WO 2006/136606 A2 | 12/2006 |
| WO | WO 2008/034039 A2 | 3/2008 |
| WO | WO 2011076786 A1 * | 6/2011 |

OTHER PUBLICATIONS

Wade, M., et al. "Targeting Mdm2 and Mdmx in Cancer Therapy: Better Living through Medicinal Chemistry?" Mol. Cancer Res. 2009; 7: pp. 1-11.*
Sun, T., et al. "Single-Nucleotide Polymorphisms in p53 Pathway and Aggressiveness of Prostate Cancer in a Caucasian Population." Clin. Cancer Res. 2010; 16: 5244-5251.*
American Cancer Society. "Leukemia—Acute Myeloid (Myelogenous)." © 2013. Available from: < http://www.cancer.org/cancer/leukemia-acutemyeloidaml/detailedguide/leukemia-acute-myeloid-myelogenous-what-is-aml >.*
National Cancer Institute. "Drugs Approved for Leukemia." © 2013. Available from: < http://www.cancer.gov/cancertopics/druginfo/leukemia/print >.*
Chen, R. et al., "Ytterbium(III) Triflate-Catalyzed Stereoselective Synthesis of Beta-lactams via [2+2] Cyclocondensation in Ionic Liquid," Synthetic Communications, 36(21):3167-3174, Taylor & Francis Group, LLC (English)(2006).
Ivanov, I. et al., "Polyphosphoric Acid-Induced Construction of Quinazolinone Skeleton from 1-(3,4-Dimethoxyphenyl)-3-Phenylurea and Carboxylic Acids," Heterocycles, 68(7):1443-1449, The Japan Institute of Heterocyclic Chemistry (English)(2006).
Mollov, N.M. et al., "Internal Alpha-Amidoalkylation Leading to 1,4-Dihydro-3(2H)-Isoquinolinones," Acta Chimica Academiae Scientiarum Hungaricae, 98(3):315-19 (English)(1978).
Mollov, N.M. et al., "Reactivity of Adducts Obtained from Arylacetyl Chloride and Aromatic Schiff Bases," Izvestiya po Khimiya, 10(4):616-20 (English)(1977).
Pfeiffer, P. et al., "Autoxidation Phenomena in the Anils of the Indandione Series. II," Journal fuer Praktische Chemie (Leipzig), 159:13-35 (1941)[Abstract and Article].
Pfeiffer, P. et al., "Autoxidation Phenomena. VI," Justus Liebigs Annalen der Chemie, 563:73-85 (1949)[Abstract and Article].
Pfeiffer, P. et al., "Autoxidation Reactions. VII," Justus Liebigs Annalen der Chemie, 581:149-59 (1953)[Abstract and Article].
Richter, D., "Anthraquinone Coloring Matters: Ruberythric Acid," Journal of the Chemical Society, 1701-3 (1936).
Schonberg, A. et al., "Autoxidation Phenomena and Valency Tautomerism in the Indone Series," Journal of the Chemical Society, 109-12 (1937).
Venkov, A. et al., "An Improved Synthesis of N-Substituted 1-Aryl-3-Oxo-1,2,3,4-Tetrahydroisoquinolines," Synthesis, 216-17, Stuttgart, New York (English)(1982).

(Continued)

*Primary Examiner* — Noble Jarrell
*Assistant Examiner* — John S Kenyon
(74) *Attorney, Agent, or Firm* — Michelle Han; Matthew E. Mulkeen

(57) ABSTRACT

A crystalline form of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one, which is useful in the treatment of a disease or disorder associated with the interaction between p53, or variants thereof, and MDM2 and/or MDM4, or variants thereof, respectively.

3 Claims, 2 Drawing Sheets

(56) References Cited

OTHER PUBLICATIONS

Yamamoto, M. et al., "Synthetic Studies on Quinazoline Derivatives. II. The Reactions of 2-Trichloro- and 2-Trifluoroacetamidobenzophenones with Primary Amines," Chemical & Pharmaceutical Bulletin, 29(8):2135-56 (English)(1981).

Zhang, Y. et al., "Superacid-Promoted Reactions of N-Acyliminium Ions: An Effective Route to Substituted 3-Oxo-1,2,3,4-Tetrahydroisoquinolines and Related Products," Synthesis (11):1775-1780 (English)(2006).

Acharya, B. P. et al., "Friedel-Crafts Acylation with 2-Isocyanatobenzoyl Chlorides: The Structure of the Intermediate Complex," Journal of Chemical Research, Synopses (4): 96-7 (1987) [Abstract only].

Bahloul, A. et al., "1.3-Dipolar Cycloaddition of Diarylnitrilimines with 4-Arylidene-1,2-Diphenyl-1.4-Dihydro-3(2H)-Isoquinolin-3-Ones," Journal de la Societe Marocaine de Chimie, 2(1): 12-17 (French) (1993) [Abstract only].

Dietz, G. et al., "Synthesis and Conversion of 3,4-Dihydroquinazolin-4-ols. Part 2: Conversion of 3,4-Dihydroquinazolin-4-ols," Direktionsber. Forsch. Entwicki. VEB Pharm. Komb. Germed Dresden, Dresden, Ger. Dem. Rep. Pharmazie, 35(12): 751-5 (German) (1980) [Abstract only].

Ishiwaka, N. et al., "Aminobenzophenone Derivatives V. Reactions of 2-Amino-5-Chloro-Benzophenone with Isocyanates and Isothiocyanates." Kagaku Zasshi, 90(9): 917-20 (Japanese) (1969) [Abstract only].

Ishiwaka, N. et al., "Reaction of 2-Amino-5-Chlorobenzophenone with P-Substituted Phenyl Isocyanates," Kagaku Zasshi, 91(10): 994-7 (Japanese) (1970) [Abstract only].

Ivanov, I., "Synthesis of 6,7-Dimethoxy-3,4-Diphenyl-2(1H)-Quinazolinone from 1-(3,4-Dimethoxyphenyl)Urea and Bonzoic Acid in Polyphoshoric Acid," Molbank M492/1-M492/2 (English) (2006) [Abstract only].

Mollv, N.M. et al., "Synthesis of 3(2H)-isoquinolinones by Means of Inner Alpha-Amidoalkylation," Doklady Bolgarskoi Akademii Nauk, 28(8): 1055-7 (English) (1975) [Abstract only].

Mumm, O. et al. "Diacylamides." Berichte der Deutschen Chemischen Gesellschaft. 48: 379-91 (1915) [Abstract only].

Richter, P. et al., "Synthesis of Derivatives of 2-Hydrazino-1,4- or 3,4-Dihydroquinazolines," Pharmazie, 45(10): 721-4 (German) (1990) [Abstract only].

Schonberg, A. et al. "Autoxidation Effects in the Indone Series." Naturwissenschaften, 24: 620 (1936) [Abstract only].

Ventsov, A. et al., Synthesis of N-Substituted 1, 4-Dihydro-3(2H)-Isoquinolinones from 3,4,5-Trimethoxyphenylacetyl chloride and Schiff Bases, Bolgarskoi Akademii Nauk, 34 (10): 1405-7 (English) (1981) [Abstract only].

Zin'Kovskaya, V.R. et al., "Ring-chain transformations involving the carbonyl group. XVI. Amides of 2-benzoylphenyl-Alpha, Alpha-dimethylacetic acid," Latvijas PSR Zinatnu, Akademijas Vestis, Kimijas Serija, (1) 65-8 (Russian) (1976) [Abstract only].

WebMD. "Leukemia." Available from: < http://www.webmd.com/cancer/tc/leukemia-prevention?print=true# >. © 2010.

Mayo Clinic "Leukemia Medications." Available from: < http://www.drugs.com/condition/leukemia.html >. © 2013.

Wade, M., et al. "Targeting Mdm2 and Mdmx in Cancer Therapy: Better Living through Medicinal Chemistry?" Mol. Cancer, Res. 2009;7:pp. 1-11.

Sun, T., et al. "Single-Nucleotide Polymorphisms in p53 Pathway and Aggressiveness of Prostate Cancer in a Caucasian Population," Clin. Cancer Res. 2010, 16: 5244-5251.

* cited by examiner

CRYSTALLINE FORM OF AN INHIBITOR OF MDM2/4 AND P53 INTERACTION

FIELD OF THE INVENTION

The present invention relates to a crystalline form of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one sulphate salt, which is useful in the treatment of a disease or disorder associated with the interaction between p53, or variants thereof, and MDM2 and/or MDM4, or variants thereof, respectively, especially binding to MDM2 and/or MDM4, or variants thereof, a process for the preparation of the crystalline form, pharmaceutical preparations comprising the crystalline form, uses and methods of use for such crystalline form in treatment of a disease or disorder (including therapy and/or prophylaxis), and/or related subject matter as specified below.

p53 refers to all genes and/or proteins encoded thereof with the names TP53, p53, TP73, p73, TP63, TP73L, p63. MDM2 refers to all genes and/or proteins encoded thereof with the names MDM2, Mdm2, HDM2, Hdm2. MDM4 refers to all genes and/or proteins encoded thereof with the names MDM4, Mdm4, HDM4, Hdm4, MDMX, MdmX, HDMX, HdmX.

Protein p53 is known as a tumor suppressor protein which helps to control cellular integrity and prevents the proliferation of permanently damaged cells by initiating, among other responses, growth arrest or apoptosis (controlled cell death). p53 mediates its effects in that it is a transcription factor capable of regulating a number of genes that regulate e.g. cell cycle and apoptosis. Thus, p53 is an important cell cycle inhibitor. These activities are tightly controlled by MDM2, an important negative regulator of the p53 tumor suppressor. "MDM2" (originally from the oncogene "murine double minute 2") refers both to the name of the gene as well as the protein encoded by that gene. MDM2 protein functions both as an E3 ubiquitin ligase that recognizes the N-terminal trans-activation domain (TAD) of the p53 tumor suppressor and thus mediates the ubiquitin-dependent degradation of p53, and as an inhibitor of p53 transcriptional activation.

The original mouse oncogene, which codes for the MDM2 protein, was originally cloned from a transformed mouse cell line. The human homologue of this protein was later identified and is sometimes also called HDM2 (for "human double minute 2"). Further supporting the role of MDM2 as an oncogene, several human tumor and proliferative disease types have been shown to have increased levels of MDM2, including inter alia soft tissue sarcomas, bone cancer, e.g. osteosarcomas, breast tumors, bladder cancer, Li-Fraumeni syndrome, brain tumor, rhabdomyosarcoma and adrenocortical carcinoma and the like. Another protein belonging to the MDM2 family is MDM4, also known as MDMX.

Dysregulation of the MDM2/p53 ratio, e.g. due to mutations, polymorphisms or molecular defects in the affected cells, can thus be found in many proliferative diseases. MDM2, in view of its mentioned effects, is capable to inhibit the activity of the tumor suppressor protein p53, thus leading to loss of p53's tumor suppressor activity and inhibiting regulatory mechanisms that impede cells from uncontrolled proliferation. As a consequence, uncontrolled proliferation can take place, leading to tumors, leukemias or other proliferative diseases.

Reference herein to inhibition of the MDM2/p53 interaction includes MDM2/p53 interaction and/or MDM4/p53 interaction herein, in particular Hdm2/p53 and/or Hdm4/p53 interaction.

There is a need for a crystalline form of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one, which is useful in providing a pharmaceutical composition for use in treating diseases or disorders associated with MDM2/p53 interaction.

BRIEF SUMMARY OF THE INVENTION

It has been found that the crystalline form I of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one sulphate salt as described herein provides a significant improvement in processing properties compared to the free base amorphous form, and provides improvements in solubility and stability.

DETAILED DESCRIPTION OF THE INVENTION

In one embodiment there is provided a crystalline form of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one sulphate salt. In particular, the sulphate salt is the bisulphate salt.

In another embodiment there is provided a crystalline form of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one bisulphate salt having a powder X ray diffraction pattern using Cu Kα radiation which includes the peaks: 18.8, 21.3 and 22.7 angle 2-Theta ° with an error+/−0.2°.

In another embodiment the invention provides a crystalline form of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one bisulphate salt having a powder X ray diffraction pattern using Cu Kα radiation which is substantially the same as as the powder X ray diffraction pattern shown in FIG. 1, or in FIG. 2, herein In further separate embodiments, the invention provides:
A crystalline form as defined in herein for use as pharmaceutical.
A crystalline form as defined herein, for use in the treatment of a disorder or a disease mediated by the activity of MDM2 and/or MDM4.
the use of a crystalline form as defined herein, for the manufacture of a medicament for the treatment of a disorder or a disease in a subject mediated by the activity of MDM2 and/or MDM4.
A pharmaceutical composition comprising a therapeutically effective amount of a crystalline form as defined herein, and one or more pharmaceutically acceptable carriers.
A method of modulating MDM2 and/or MDM4 activity in a subject, comprising the step of administering to a subject a therapeutically effective amount of a crystalline form as defined herein.
A method for the treatment of a disorder or a disease mediated by the activity of MDM2 and/or MDM4 comprising the step of administering to a subject a therapeutically effective amount of a crystalline form as defined herein.

A crystalline form, use or method as described herein, wherein the disorder or a disease is a proliferative disorder or disease.

A crystalline form as defined herein, in combination with one or more therapeutically active agents.

DEFINITIONS

As already indicated above, MDM2 (especially when mentioned as MDM2 or variants thereof) generally refers to all genes and/or proteins encoded thereof with the names MDM2, Mdm2, HDM2, Hdm2, or a variant thereof. MDM4 (especially when mentioned as MDM4 or variants thereof) refers to all genes and/or proteins encoded thereof with the names MDM4, Mdm4, HDM4, Hdm4, MDMX, MdmX, HDMX, HdmX, or a variant thereof.

MDM2 specifically relates to MDM2 as described in EMBO J. 10, 1565-9, Fakharzadeh et al., 1991, a variant thereof refers to a variant thereof which still binds to p53 in the assay system described below (e.g. a splice variant, isoform, fragment, mutant or oncogene due to deletion, insertion and/or exchange of one or more, e.g. one to 430, of the amino acids), corresponding to the full length proteins as originally described, preferably at least with 0.5%, more preferably at least with 5%, 10%, 20%, 30%, 40% or especially 50% or more of the affinity of MDM2 to p53, and have at least 20%, more preferably at least 25%, sequence identity to MDM2 or to HDM2 as originally described or as mentioned below specifically. Where not mentioned otherwise, MDM2 generally relates to MDM2, Mdm2, HDM2 or Hdm2, or variants thereof, respectively, as just defined.

MDM4 specifically relates to MDM4 as described in Genomics 43, 34-42, Shvarts et al., 1997, a variant thereof refers to a variant thereof which still binds to p53 in the assay system described below (e.g. a splice variant, isoform, fragment, mutant or oncogene due to deletion, insertion and/or exchange of one or more, e.g. one to 430, of the amino acids), corresponding to the full length proteins as originally described, preferably at least with 0.5%, more preferably at least with 5%, 10%, 20%, 30%, 40% or especially 50% or more of the affinity of MDM4 to p53, and have at least 20%, more preferably at least 25%, sequence identity to MDM4, to MDMX, to HDM4 or to HDM2 as originally described or as mentioned below specifically. Where not mentioned otherwise, MDM4 generally relates to MDM4, Mdm4, HDM4, Hdm4, MDMX, MdmX, HDMX or HdmX, or variants thereof, respectively, as just defined.

"Variants thereof" where mentioned means one or more variant(s).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

By "combination", there is meant either a fixed combination in one dosage unit form, or a kit of parts for the combined administration where a compound of the formula (I) and a combination partner may be administered independently at the same time or separately within time intervals that especially allow that the combination partners show a cooperative, e.g. synergistic effect.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by the dysregulation of the p53/MDM2 ratio, or (ii) associated with the dysregulation of the p53/MDM2 ratio, or (iii) characterized by the dysregulation of the MDM2/p53 ratio; or (2) reducing or inhibiting the activity of the p53/MDM2 interaction. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the p53/MDM2 interaction.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

"Sulphate salt" can mean the bisulphate salt, or the monosulphate salt, or mixtures thereof.

Pharmaceutical Compositions

The invention also relates to pharmaceutical compositions comprising a crystalline form of the present invention. The invention thus provides a pharmaceutical composition comprising (i.e. containing or consisting of) the crystalline form as defined herein and one or more carriers/excipients;

a pharmaceutical composition comprising a therapeutically effective amount of the crystalline form as defined herein, and one or more pharmaceutically acceptable carriers/excipients.

The present invention provides a pharmaceutical composition comprising a the crystalline form of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Pharmaceutical Uses

The invention relates in another aspect to the use of the crystalline form of the present invention as pharmaceuticals. The invention thus provides:

the crystalline form as defined herein for use as a medicament;

the crystalline form of the present invention for use in the treatment of a disorder or a disease in a subject associated with the activity of MDM2 and/or MDM4;

the use of the crystalline form of the present invention, in the manufacture of a medicament for the treatment of a disorder or a disease in a subject associated with the activity of MDM2 and/or MDM4;

the use of the crystalline form as defined herein, for the treatment of a proliferative disorder or disease selected from cancer or tumor diseases, such as benign or malignant tumors, a sarcoma, such as liposarcoma, rhabdomyosarcoma or bone cancer, e.g. osteosarcomas, a carcinoma, such as of the brain, kidney, liver, adrenal gland, bladder, breast, gastric, ovary, colon, rectum, prostate, pancreas, lung, vagina or thyroid, a glioblastoma, a multiple myeloma, a gastrointestinal cancer, especially colon carcinoma or colorectal adenoma, a tumor of the head and neck, a melanoma, a prostate hyperplasia, a neoplasia, a neoplasia of epithelial character, a leukemia or a lymphoma, such as of B- or T-cell origin, and metastases in other organs), viral infections (e.g. herpes, papilloma, HIV, Kaposi's, viral hepatitis);

a method of modulating of MDM2 and/or MDM4 activity in a subject, comprising the step of administering to a subject a therapeutically effective amount of the crystalline form of the present invention;

a method for the treatment of a disorder or a disease associated with the activity of MDM2 and/or MDM4 comprising the step of administering to a subject a therapeutically effective amount of the crystalline form of the present invention as described herein;

The efficacy of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one can be demonstrated as shown in WO 98/01467 (which especially regarding the assays is included herein by reference) or preferably follows:

Time Resolved Fluorescence Energy Transfer (TR-FRET) Assay

The inhibition of p53-Hdm2 and p53-Hdm4 interactions is measured by time resolved fluorescence energy transfer (TR-FRET). Fluorescence energy transfer (or Foerster resonance energy transfer) describes an energy transfer between donor and acceptor fluorescent molecules. For this assay, MDM2 protein (amino acids 2-188) and MDM4 protein (amino acids 2-185), tagged with a C-terminal Biotin moiety, are used in combination with a Europium labeled streptavidin (Perkin Elmer, Inc., Waltham, Mass., USA) serving as the donor fluorophore. The p53 derived, Cy5 labeled peptide Cy5-TFS-DLWKLL (p53 aa18-26) is the energy acceptor. Upon excitation of the donor molecule at 340 nm, binding interaction between MDM2 or MDM4 and the p53 peptide induces energy transfer and enhanced response at the acceptor emission wavelength at 665 nm. Disruption of the formation of the p53-MDM2 or p53-MDM4 complex due to an inhibitor molecule binding to the p53 binding site of MDM2 or MDM4 results in increased donor emission at 615 nm. The ratiometric FRET assay readout is calculated from the raw data of the two distinct fluorescence signals measured in time resolved mode (countrate 665 nm/countrate 615 nm×1000).

The test is performed in white 1536 w microtiterplates (Greiner Bio-One GmbH, Frickenhausen, Germany) in a total volume of 3.1 µl by combining 100 nl of compounds diluted in 90% DMSO/10% $H_2O$ (3.2% final DMSO concentration) with 2 µl Europium labeled streptavidin (final concentration 2.5 nM) in reaction buffer (PBS, 125 mM NaCl, 0.001% Novexin (consists of carbohydrate polymers (Novexin polymers), designed to increase the solubility and stability of proteins; Novexin Ltd., Cambridgeshire, United Kingdom), Gelatin 0.01%, 0.2% Pluronic (block copolymer from ethylenoxide and propyleneoxide, BASF, Ludwigshafen, Germany), 1 mM DTT), followed by the addition of 0.5 µl MDM2-Bio or MDM4-Bio diluted in assay buffer (final concentration 10 nM). Allow the solution to pre-incubate for 15 minutes at room temperature, followed by addition of 0.5 µl Cy5-p53 peptide in assay buffer (final concentration 20 nM). Incubate at room temperature for 10 minutes prior to reading the plate. For measurement of samples, an Analyst GT multimode microplate reader (Molecular Devices) with the following settings is used: Dichroic mirror 380 nm, Excitation 330 nm, Emission Donor 615 nm and Emission Acceptor 665 nm. 1050 values are calculated by curve fitting using XLfit. If not specified, reagents are purchased from Sigma Chemical Co, St. Louis, Mo., USA.

There are also experiments that can demonstrate the anti-tumor activity of compounds of the formula (I) in vivo.

For example, female Harlan (Indianapolis, Ind., USA) athymic nu/nu mice with s.c. transplanted human osteosarcoma SJSA-1 tumors can be used to determine the anti-tumor activity of p53/MDM2 interaction inhibitors. On day 0, with the animals under peroral Forene® (1-chloro-2,2,2-trifluoro-ethyldifluormethylether, Abbot, Wiesbaden, Germany) narcosis, $3 \times 10^6$ cells are injected under the skin on the animals' left flank. When tumors reach a volume of 100 $mm^3$, the mice are divided at random into groups of 6-8 animals and treatment commences. The treatment is carried out for a 2-3 weeks period with peroral, intravenous or intra-peritoneal administration twice daily (or less frequently) of a compound of the formula (I) in a suitable vehicle at defined doses. The tumors are measured twice a week with a slide gauge and the volume of the tumors is calculated.

As an alternative to cell line SJSA-1, other cell lines may also be used in the same manner, for example, the HCT116 colon carcinoma cell line (ATCC No. CCL-247);

the LNCaP clone FGC prostate carcinoma cell line (ATCC No. CRL-1740);

the RKO colon carcinoma cell line (ATCC No. CRL-2577);

the HT1080 fibrosarcoma cell line (ATCC No. CCL-121);

the A375 malignant melanoma cell line (ATCC No. CRL-1619), the NCI-H460 large cell lung carcinoma cell line (ATCC No. HTB-177);

the JEG-3 choriocarcinoma (ATCC No. HTB-36)

the ZR-75-1 breast ductal carcinoma (ATCC No. CRL-1500)

((S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one free base:
$IC_{50}$ (μM) of p53-Hdm2 inhibition (TR-FRET) Assay: 0.0008
$IC_{50}$ (μM) of p53-Hdm4 inhibition (TR-FRET) Assay: 2.10
((S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one bisulphate salt as disclosed herein:
$IC_{50}$ (μM) of p53-Hdm2 inhibition (TR-FRET) Assay: 0.0019
$IC_{50}$ (μM) of p53-Hdm4 inhibition (TR-FRET) Assay: 2.2

Combinations

The invention relates in another aspect to combinations comprising the crystalline form of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one as described herein, and one or more additional active ingredients. The invention thus provides:
- a combination in particular a pharmaceutical combination, comprising the crystalline form of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one as described herein, and one or more therapeutically active agents, particularly antiproliferative agents;
- a combined pharmaceutical composition, adapted for simultaneous or sequential administration, comprising the crystalline form of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one as described herein; therapeutically effective amount(s) of one or more combination partners, particularly antiproliferative agents; one or more pharmaceutically acceptable excipients;
- a combined pharmaceutical composition as defined herein (i) as pharmaceutical, (ii) for use in the treatment of a disorder or a disease mediated by the activity of MDM2 and/or MDM4, (iii) in a method of treatment of a disorder or a disease mediated by the activity of MDM2 and/or MDM4.

The crystalline form of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one as described herein may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibittors; mTOR inhibitors, such as RAD001; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies, such as HCD122; heparanase inhibitors; inhibitors of Ras oncogenic isoforms; telomerase inhibitors; proteasome inhibitors; compounds used in the treatment of hematologic malignancies, such as fludarabine; compounds which target, decrease or inhibit the activity of Flt-3, such as PKC412; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics and AUY922; temozolomide (TEMODAL™); kinesin spindle protein inhibitors, such as SB715992 or SB743921 from GlaxoSmithKline, or pentamidine/chlorpromazine from CombinatoRx; PI3K inhibitors, such as BEZ235; RAF inhibitors, such as RAF265; MEK inhibitors such as ARRY 142886 from Array PioPharma, AZD6244 from AstraZeneca, PD181461 from Pfizer, leucovorin, EDG binders, antileukemia compounds, ribonucleotide reductase inhibittors, S-adenosylmethionine decarboxylase inhibitors, regulators of apoptosis, antiproliferative antibodies or other chemotherapeutic compounds. Further, alternatively or in addition they may be used in combination with other tumor treatment approaches, including surgery, ionizing radiation, photodynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSAID or antagonists of chemokine receptors.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX™), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL™. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "antineoplastic antimetabolite" includes, but is not limited to, 5-Fluorouracil or 5-FU, capecitabine, gemcitabine, DNA demethylating compounds, such as 5-azacytidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity"; or "further anti-angiogenic compounds" as used herein includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;

d) compounds targeting, decreasing or inhibiting the activity of the Trk receptor tyrosine kinase family, or ephrin B4 inhibitors;

e) compounds targeting, decreasing or inhibiting the activity of the Axl receptor tyrosine kinase family;

f) compounds targeting, decreasing or inhibiting the activity of the Ret receptor tyrosine kinase;

g) compounds targeting, decreasing or inhibiting the activity of the Kit/SCFR receptor tyrosine kinase, i.e C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;

h) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825)

i) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; BEZ235 (a PI3K inhibitor) or AT7519 (CDK inhibitor);

j) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC™) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);

k) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin™) cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and l) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF;

m) compounds targeting, decreasing or inhibiting the activity of PI3K, such as BEZ235 or BKM120;

n) compounds targeting, decreasing or inhibiting the activity of the cyclin dependent kinase family, such as PD 0332991.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g. inhibitors of phosphatase 1, phosphatase 2A, or CDC25, e.g. okadaic acid or a derivative thereof.

Compounds which induce cell differentiation processes are e.g. retinoic acid, α- γ- or δ-tocopherol or α- γ- or δ-tocotrienol.

The term cyclooxygenase inhibitor as used herein includes, but is not limited to, e.g. Cox-2 inhibitors, 5-alkyl substituted 2-arylaminophenylacetic acid and derivatives, such as celecoxib (CELEBREX™), rofecoxib (VIOXX™), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune™), everolimus (Certican™ or Afinitor™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetrazolyle derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g. PKC412, TKI258, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino,17-demethoxygeldanamycin (17AAG), a geldanamycin derivative; other geldanamycin related compounds; radicicol and HDAC inhibitors. An example HSP90 inhibitor is AUY922.

The term "regulators of apoptosis" as used herein includes, but is not limited to, compounds targeting, decreasing or inhibiting the activity of Bcl2 family members (such as ABT-263) and IAP family members (such as AEG40826); or inducing apoptosis by known or unknown mechanism(s) of action (e.g. TRAIL antibody, DR5 antibody).

The term "antiproliferative antibodies" as used herein includes, but is not limited to, trastuzumab (Herceptin™), Trastuzumab-DM1, erbitux, bevacizumab (Avastin™) rituximab (Rituxan™), PRO64553 (anti-CD40), 2C4 Antibody and HCD122 antibody (anti-CD40). By antibodies is meant e.g. intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), the solid form of the invention herein can be used in combination with standard leukemia therapies, especially in combination with therapies used for the treatment of AML. In particular, said solid form can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The term "antileukemic compounds" includes, for example, Ara-C, a pyrimidine analog, which is the 2"-alpha-hydroxy ribose (arabinoside) derivative of deoxycytidine. Also included is the purine analog of hypoxanthine, 6-mercaptopurine (6-MP) and fludarabine phosphate.

Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A, LDH589 disclosed in WO 02/22577 and compounds disclosed in U.S. Pat. No. 6,552,065, in particular, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]amino]methyl]phenyl}-2E-2-propenamide, or a pharmaceutically acceptable salt thereof, especially the lactate salt.

Somatostatin receptor antagonists as used herein refer to compounds which target, treat or inhibit the somatostatin receptor such as octreotide, and SOM230 (pasireotide).

Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., 4th Edition, Vol. 1, pp. 248-275 (1993).

The term "EDG binders" as used herein refers a class of immunosuppressants that modulates lymphocyte recirculation, such as FTY720.

The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica*, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, *Cancer Res*, Vol. 59, pp. 5209-5218 (1999); Yuan et al., *Proc Natl Aced Sci USA*, Vol. 93, pp. 14765-14770 (1996); Zhu et al., *Cancer Res*, Vol. 58, pp. 3209-3214 (1998); and Mordenti et al., *Toxicol Pathol*, Vol. 27, No. 1, pp. 14-21 (1999); in WO 00/37502 and WO 94/10202; ANGIOSTATIN, described by O'Reilly et al., *Cell*, Vol. 79, pp. 315-328 (1994); ENDOSTATIN, described by O'Reilly et al., *Cell*, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin™)

Photodynamic therapy as used herein refers to therapy which uses certain chemicals known as photosensitizing compounds to treat or prevent cancers. Examples of photodynamic therapy include treatment with compounds, such as e.g. VISUDYNE™ and porfimer sodium.

Angiostatic steroids as used herein refers to compounds which block or inhibit angiogenesis, such as, e.g., anecortave, triamcinolone. hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as e.g. fluocinolone, dexamethasone.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code nos., generic or trade names may be taken from the actual edition of the standard compendium "The Merck Index" or from databases, e.g. Patents International (e.g. IMS World Publications).

None of the quotations of references made within the present disclosure is to be understood as an admission that the references cited are prior art that would negatively affect the patentability of the present invention.

The above-mentioned compounds, which can be used in combination with the crystalline form of (S)-1-(4-Chlorophenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one as described herein, can be prepared and administered as described in the art.

Administration

The invention also provides a pharmaceutical preparation, comprising the crystalline form of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one as described herein, and at least one pharmaceutically acceptable carrier.

Said crystalline form as described herein can be administered alone or in combination with one or more other therapeutic compounds, possible combination therapy taking the form of fixed combinations or the administration of a compound of the invention and one or more other therapeutic (including prophylactic) compounds being staggered or given independently of one another, or the combined administration of fixed combinations and one or more other therapeutic compounds. Said solid form can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

The dosage of the active ingredient depends upon a variety of factors including type, species, age, weight, sex and medical condition of the patient; the severity of the condition to be treated; the route of administration; the renal and hepatic function of the patient; and the particular compound employed. A physician, clinician or veterinarian of ordinary skill can readily determine and prescribe the effective amount of the drug required to prevent, counter or arrest the progress of the condition. Optimal precision in achieving concentration of drug within the range that yields efficacy requires a regimen based on the kinetics of the drug's availability to target sites. This involves a consideration of the distribution, equilibrium, and elimination of a drug.

The dose of the crystalline form of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one as described herein to be administered to warm-blooded animals, for example humans of approximately 70 kg body weight, is preferably from approximately 3 mg to approximately 15 g, more preferably from approximately 10 mg to approximately 3 g, yet more preferably from approximately 50 mg to 1.5 g per person per day, undivided in 1 dose or divided preferably into 2 to 4, e.g. 2 or 3, single doses which may, for example, be of the same size. Usually, children receive half of the adult dose.

Said solid form may be administered by any conventional route, in particular parenterally, for example in the form of injectable solutions or suspensions, enterally, e.g. orally, for example in the form of tablets or capsules, topically, e.g. in the form of lotions, gels, ointments or creams, or in a nasal or a suppository form. Topical administration is e.g. to the skin. A further form of topical administration is to the eye. Pharmaceutical compositions comprising a compound of the invention in association with at least one pharmaceutical acceptable carrier or diluent may be manufactured in conventional manner by mixing with a pharmaceutically acceptable carrier or diluent.

The invention relates also to pharmaceutical compositions comprising an effective amount, especially an amount effective in the treatment of one of the above-mentioned disorders, of the crystalline form of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one as described herein together with one or more pharmaceutically acceptable carriers that are suitable for topical, enteral, for example oral or rectal, or parenteral administration and that may be inorganic or organic, solid or liquid.

There can be used for oral administration especially tablets or gelatin capsules that comprise the active ingredient together with diluents, for example lactose, dextrose, mannitol, and/or glycerol, and/or lubricants and/or polyethylene glycol. Tablets may also comprise binders, for example magnesium aluminum silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavorings and sweeteners. It is also possible to use the pharmacologically active compounds of the present invention in the form of parenterally administrable compositions or in the form of infusion solutions. The pharmaceutical compositions may be sterilized and/or may comprise excipients, for example preservatives, stabilisers, wetting compounds and/or emulsifiers, solubilisers, salts for regulating the osmotic pressure and/or buffers. The present pharmaceutical compositions, which may, if desired, comprise other pharmacologically active substances are prepared in a manner known per se, for example by means of conventional mixing, granulating, confectionning, dissolving or lyophilising processes, and comprise approximately from 1% to 99%, especially from approximately 1% to approximately 20%, active ingredient(s).

Synthetic Route

Example 106

(S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one

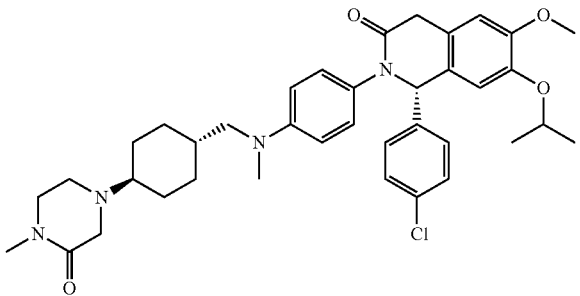 [SMILES: COc1cc2c(cc1OC(C)C)[C@H](c1ccc(Cl)cc1)N(c1ccc(N(C)C[C@H]3CC[C@H](N4CCN(C)C(=O)C4)CC3)cc1)C(=O)C2]

A sealable reaction flask was charged with potassium phosphate (4.44 g, 20.29 mmol), evacuated and heated for 15 min at 170° C. The reaction flask was back-filled with argon at RT and Intermediate 75.6 (3.64 g, 10.15 mmol), Intermediate 106.1 (5.48 g, 12.18 mmol), dioxan (75 mL) and (+/−)-trans-1,2-diaminocyclohexane (0.37 mL, 3.04 mmol) were added subsequently. The reaction flask was carefully evacuated under vacuum (2×) and backfilled with argon (2×) and copper (I) iodide (0.586 g, 3.04 mmol) were added. The reaction mixture was stirred for 22.5 h at 95° C. The mixture was extracted between EtOAc (3×) and water (3×). The organic phases were washed with brine and dried over $Na_2SO_4$, filtered and evaporated to dryness. Purification of the residue by normal phase column chromatography, eluting with 100% EtOAc to 20% MeOH/EtOAc followed by reverse phase prep-HPLC afforded the TFA salt which was extracted between EtOAc (2×) and 1M aqueous $NaHCO_3$ (1×). The organic phases were washed with brine and dried over Na$_2$SO$_4$, filtered and evaporated to dryness gave the title compound as white solid (1.59 g, 2.41 mmol, 23.8%): HPLC: $^E$t$_{Ret}$=4.57 min; LC-MS: m/z 659.2 [M+H]$^+$; 1H NMR (400 MHz, DMSO-d$_6$) 0.88-1.01 (m, 2H) 1.05-1.14 (m, 2H) 1.16 (d, J=5.86 Hz, 3H) 1.21 (d, J=6.25 Hz, 3H) 1.48-1.62 (m, 1H) 1.73 (dd, 4H) 2.14-2.27 (m, 1H) 2.65 (t, J=5.47 Hz, 2H) 2.76 (s, 3H) 2.85 (s, 3H) 3.02 (s, 2H) 3.06-3.20 (m, 4H) 3.54 (d, 1H) 3.71 (s, 3H) 3.87 (d, J=19.53 Hz, 1H) 4.39-4.47 (m, 1H) 5.92 (s, 1H) 6.54 (d, 2H) 6.81 (s, 1H) 6.87 (d, 2H) 7.02 (s, 1H) 7.33 (s, 4H).

Intermediate 106.1: 4-(4-{[(4-Iodo-phenyl)-methyl-amino]-methyl}-trans-cyclohexyl)-1-methyl-piperazin-2-one

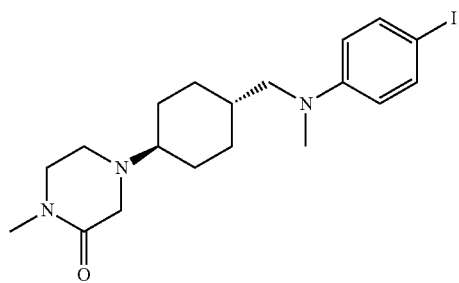 [SMILES: CN1CCN([C@H]2CC[C@H](CN(C)c3ccc(I)cc3)CC2)CC1=O]

To a solution of Intermediate 106.2 (13.3 g, 20.9 mmol) in dioxane (52.3 mL) was added 4M dioxane solution of HCl (105 mL, 418 mmol) at 0° C. The reaction mixture was stirred at RT for 0.5 h. The solution was concentrated and the residue was dissolved in MeOH (157 mL), triethylamine (27.3 ml, 196 mmol) was added drop wise at 0° C. and the mixture was stirred for 1 h at RT. The reaction mixture was concentrated and the residue extracted between EtOAc (2×) and 1M aqueous NaHCO$_3$ (1×). The organic phases were washed with brine and dried over Mg$_2$SO$_4$, filtered and evaporated to dryness. The cure material was suspended in Et$_2$O (50 mL), and after stirring and sonication during 30 min, it was filtered on paper, washed with Et$_2$O (50 mL) and dryness under high vacuum to give a white powder (8.11 g, 18.0 mmol, 86%). HPLC: $^E$t$_{Ret}$=4.035 min; LC-MS: m/z 442.1 [M+H]$^+$; $^1$H NMR (400 MHz, DMSO-d$_6$) 0.84-1.02 (m, 2H) 1.02-1.12 (m, 2H) 1.52-1.60 (m, 1H) 1.60-1.84 (m, 4H) 2.16-2.27 (m, 1H) 2.65 (t, J=5.47 Hz, 2H) 2.76 (s, 3H) 2.85 (s, 3H) 3.02 (s, 2H) 3.10 (d, J=7.03 Hz, 2H) 3.14-3.20 (m, 2H) 6.47 (d, 2H) 7.37 (d, 2H).

Intermediate 106.2: [[2-(tert-Butoxycarbonyl-methyl-amino)-ethyl]-(4-{[(4-iodo-phenyl)-methyl-amino]-methyl}-trans-cyclohexyl)-amino]-acetic acid methyl ester

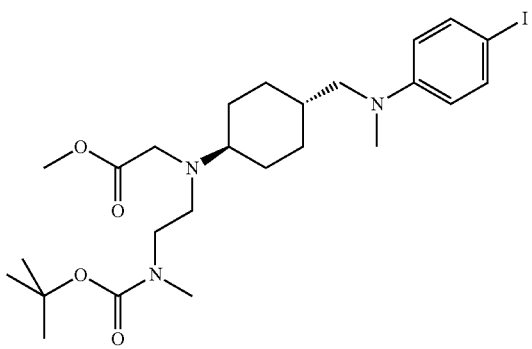 [SMILES: COC(=O)CN(CCN(C)C(=O)OC(C)(C)C)[C@H]1CC[C@H](CN(C)c2ccc(I)cc2)CC1]

To a suspension of Intermediate 105.3 (9.45 g, 21.6 mmol), methyl-(2-oxo-ethyl)-carbamic acid tert-butyl ester (4.11 g, 23.7 mmol) and AcOH (3.7 mL, 64.7 mmol) in DCM (108 mL) was added potion wise NaBH(OAc)$_3$ (13.7 g, 64.7 mmol) at 0° C. After stirring for 1 h at RT, the reaction mixture was added carefully saturated aqueous NaHCO$_3$ to pH 8 followed by extraction with DCM (2×). The organic phases were dried over Mg$_2$SO$_4$, filtered and evaporated, which gave the crude title intermediate (13.3 g, 20.9 mmol, 97% with 90% purity). This material was used for the next step without further purifications. HPLC: $^E$t$_{Ret}$=5.32 min; LC-MS: m/z 574.3 [M+H]$^+$.

Intermediate 105.3: (4-{[(4-Iodo-phenyl)-methyl-amino]-methyl}-trans-cyclohexylamino)-acetic acid methyl ester

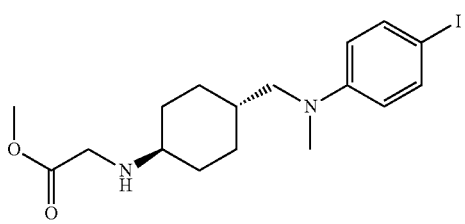 [SMILES: COC(=O)CN[C@H]1CC[C@H](CN(C)c2ccc(I)cc2)CC1]

To a solution of Intermediate 105.4 (16.9 g, 49.2 mmol) in DMF (300 mL) was successively added potassium carbonate (14.3 g, 103 mmol) and methyl 2-bromoacetate (4.77 mL, 51.7 mmol) at −10° C. The suspension was stirred for 4.5 h at −10° C. to 10° C. The reaction mixture was diluted with EtOAc, the organic phase was washed with water and brine, and dried over Na$_2$SO$_4$, filtered and evaporated to dryness. Purification of the residue by normal phase column chromatography, eluting with 100% DCM to 100% EtOAc, gave the title compound as brown oil (9.45 g, 21.6 mmol, 43.8%). HPLC: $^E$t$_{Ret}$=4.22 min; LC-MS: m/z 417.0 [M+H]$^+$.

Intermediate 105.4: (Trans-4-amino-cyclohexylmethyl)-(4-iodo-phenyl)-methyl-amine

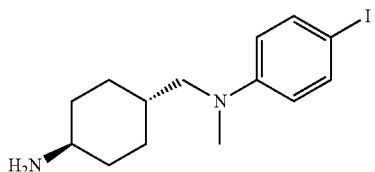

To a solution of Intermediate 77.1 (21.9 g, 49.5 mmol) in DCM (300 mL) was added drop wise TFA (114 mL, 1484 mmol) at 0° C. The reaction mixture was stirred for 30 min at RT, then concentrated in vacuo. The residue was diluted with EtOAc, and adjusted to pH 9 at 0° C. by addition of 2M NaOH. The phases were separated and water layer was extracted with EtOAc. The organic layer was washed with water and brine, dried over Na$_2$SO$_4$, and filtered. Concentration in vacuo gave the title compound as grey solid (16.9 g, 47.8 mmol, 97%). HPLC: $^E t_{Ret}$=3.92 min; LC-MS: m/z 345.1 [M+H]$^+$.

Intermediate 77.1: (4-{[(4-Iodo-phenyl)-methyl-amino]-methyl}-trans-cyclohexyl)-carbamic acid tert-butyl ester

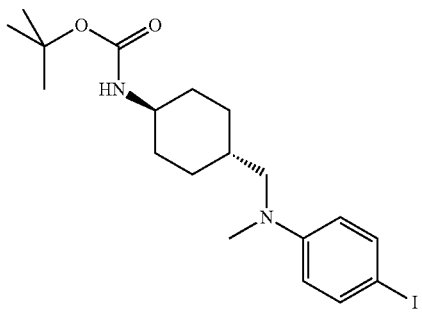 [SMILES: CN(C[C@H]1CC[C@H](NC(=O)OC(C)(C)C)CC1)c1ccc(I)cc1]

To a solution of Intermediate 75.7 (748 mg, 1.74 mmol) in DCM (15 ml) were successively added AcOH (0.199 ml, 3.48 mmol), formaldehyde (37% in water, 0.259 ml, 3.48 mmol) and NaBH(OAc)$_3$ (737 mg, 3.48 mmol) at RT. The reaction mixture was stirred at RT for 2 h then diluted with DCM and washed with a 2M aqueous Na$_2$CO$_3$ solution (2×). The organic phase was dried over Na$_2$SO$_4$, filtered and evaporated to dryness. The resulting crude material was purified by Combi-Flash Companion™ (Isco Inc.) column chromatography (SiO$_2$; gradient elution, heptane/AcOEt 98:2→7:3) to yield the title compound (584 mg, 1.31 mmol, 76%) as a colorless solid. TLC: R$_F$=0.36 (heptane/AcOEt 3:1); HPLC: $^A t_{Ret}$=2.76 min; LC-MS: m/z 445.4 [M+H]$^+$; $^1$H NMR (400 MHz, DMSO-d$_6$): 0.90-1.13 (m, 4H), 1.36 (s, 9H), 1.48-1.66 (m, 3H), 1.69-1.81 (m, 2H), 2.87 (s, 3H), 3.08-3.21 (m, 1H), 3.12 (d, J=7.1, 2H), 6.45-6.54 (m, 2H), 6.68 (d, J=8.1, 1H), 7.34-7.43 (m, 2H).

Intermediate 75.7: {4-[(4-Iodo-phenylamino)-methyl]-trans-cyclohexyl}-carbamic acid tert-butyl ester

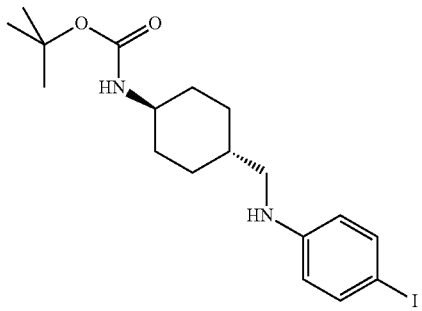 [SMILES: CC(C)(C)OC(=O)N[C@H]1CC[C@H](CNc2ccc(I)cc2)CC1]

To a solution of 4-iodo-phenylamine (1 g, 4.57 mmol) in DCM (25 ml) were successively added AcOH (0.523 ml, 9.13 mmol), (4-formyl-cyclohexyl)-carbamic acid tert-butyl ester (1.14 g, 5.02 mmol) and NaBH(OAc)$_3$ (1.94 g, 9.13 mmol) at RT. The reaction mixture was stirred at RT for 1 h then diluted with Et$_2$O and washed successively with a 2M aqueous HCl solution and a 2M aqueous Na$_2$CO$_3$ solution. The organic phase was dried over Na$_2$SO$_4$, filtered and evaporated to dryness. The resulting crude material was purified by Combi-Flash Companion™ (Isco Inc.) column chromatography (SiO$_2$; gradient elution, heptane/AcOEt 95:5→1:1) to yield the title compound (1.56 g, 3.62 mmol, 79%) as a colorless solid. TLC: R$_F$=0.72 (heptane/AcOEt 1:1); HPLC: $^A t_{Ret}$=2.64 min; LC-MS: m/z 431.4 [M+H]$^+$; $^1$H NMR (400 MHz, DMSO-d$_6$): 0.87-1.03 (m, 2H), 1.03-1.17 (m, 2H), 1.32-1.48 (m, 1H), 1.37 (s, 9H), 1.70-1.86 (m, 4H), 2.76-2.86 (m, 2H), 3.08-3.25 (m, 1H), 5.77-5.89 (m, 1H), 6.34-6.46 (m, 2H), 6.59-6.71 (m, 1H), 7.24-7.35 (m, 2H).

Intermediate 75.6: (S)-1-(4-Chloro-phenyl)-7-isopropoxy-6-methoxy-1,4-dihydro-2H-isoquinolin-3-one

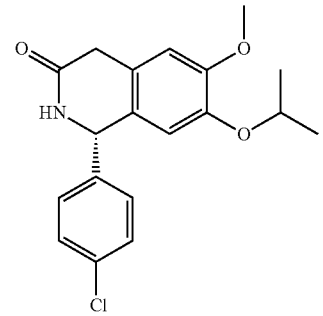 [SMILES: COc1cc2c(cc1OC(C)C)[C@H](c1ccc(Cl)cc1)NC(=O)C2]

A solution of Intermediate 75.5 (3.96 g, 7.98 mmol) in 1.25M HCl in MeOH (128 ml) was stirred at RT for 30 min. The reaction mixture was evaporated to dryness and the resulting residue was dissolved in MeOH (40 ml). Et$_3$N (5.56 ml, 39.9 mmol) was added at RT then the mixture was stirred for 15 min and evaporated to dryness. The resulting crude material was purified by Combi-Flash Companion™ (Isco Inc.) column chromatography (SiO$_2$; gradient elution, [heptane/DCM 1:1]/TBME 9:1→100% TBME) to yield the title compound (2.51 g, 7.24 mmol, 91%, ee 92%) as an off-white solid. TLC: R$_F$=0.13 (heptane/DCM/TBME 1:1:2); HPLC: $^A t_{Ret}$=2.03 min; LC-MS: m/z 346.4 [M+H]$^+$; $^1$H NMR (400 MHz, DMSO-d$_6$): 1.16 (d, J=6.1, 3H), 1.21 (d, J=6.1, 3H), 3.36 (d, J=19.8, 1H), 3.51 (d, J=19.8, 1H), 3.72 (s, 3H), 4.40 (spt, J=6.1, 1H), 5.55 (d, J=3.4, 1H), 6.79 (s, 1H), 6.84 (s, 1H), 7.26-7.33 (m, 2H), 7.35-7.42 (m, 2H), 8.49 (d, J=3.9, 1H).

Intermediate 75.5: {2-[(S)-(4-Chloro-phenyl)-((S)-2-methyl-propane-2-sulfinylamino)-methyl]-4-isopropoxy-5-methoxy-phenyl}-acetic acid ethyl ester

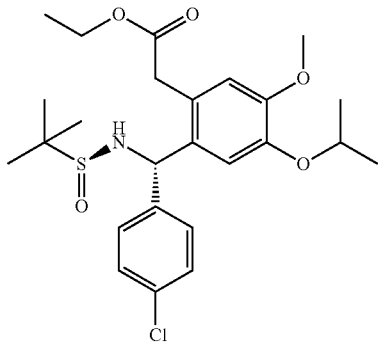 [SMILES: CCOC(=O)Cc1cc(OC)c(OC(C)C)cc1[C@@H](N[S@@](=O)C(C)(C)C)c1ccc(Cl)cc1]

A 250-mL flask was charged with Intermediate 75.3 (10.97 g, 28.6 mmol) and anhydrous THF (50 ml) then evacuated under vacuum and back-filled with argon (3×). Intermediate 75.4 (15.75 g, 57.2 mmol) and bis(acetonitrile)(1,5-cyclooctadiene)rhodium(I)tetrafluoro-borate (1.09 g, 2.86 mmol) were successively added at RT and the resulting orange suspension was heated at 60° C. and stirred for 2 h. Additional bis(acetonitrile)(1,5-cyclooctadiene)rhodium(I)tetrafluoroborate (1.09 g, 2.86 mmol) was added at 60° C. and the mixture was further stirred for 4 h. The reaction mixture was cooled to RT, diluted with AcOEt and washed with water. The organic phase was dried over $Na_2SO_4$, filtered and evaporated to dryness. The resulting crude material was purified by Combi-Flash Companion™ (Isco Inc.) column chromatography ($SiO_2$; gradient elution, heptane/AcOEt 95:5→3:7) to yield the title compound (3.96 g, 7.98 mmol, 28%) as a brownish resin. TLC: $R_F$=0.29 (heptane/AcOEt 1:1); HPLC: $^At_{Ret}$=2.70 min; LC-MS: m/z 496.3 [M+H]$^+$; $^1$H NMR (400 MHz, DMSO-$d_6$): 1.10-1.19 (m, 15H), 1.23 (d, J=5.9, 3H), 3.57 (d, J=16.4, 1H), 3.68 (d, J=16.1, 1H), 3.73 (s, 3H), 3.93-4.05 (m, 2H), 4.37-4.45 (m, 1H), 5.62 (d, J=6.1, 1H), 5.82 (d, J=6.1, 1H), 6.82 (s, 1H), 6.94 (s, 1H), 7.25-7.30 (m, 2H), 7.36-7.41 (m, 2H).

Intermediate 75.4:
(4-Chloro-phenyl)-trimethyl-stannane

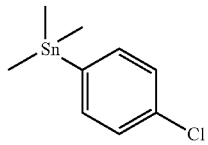

To a 1M solution of trimethyltin chloride in THF (92 ml, 92 mmol) was slowly added a 1M solution of 4-chlorophenyl-magnesium bromide in $Et_2O$ (92 ml, 92 mmol) over a 40 min period at −10° C. so that the temperature never exceed 0° C. After the addition, the cooling bath was removed and the resulting suspension was stirred at RT for 1 h. A saturated aqueous solution of $NH_4Cl$ (14 ml) was added followed by water until complete dissolution of the precipitate. The mixture was transferred into a separating funnel and extracted with $Et_2O$ (3×). The combined organic fractions were dried over $Na_2SO_4$, filtered and evaporated to dryness. The resulting crude material was purified by Combi-Flash Companion™ (Isco Inc.) column chromatography ($SiO_2$; isocratic elution with cyclohexane) to yield the title compound (24.47 g, 89 mmol, 97%) as a colorless oil. TLC: $R_F$=0.76 (cyclohexane/AcOEt 95:5); HPLC: $^At_{Ret}$=3.25 min; $^1$H NMR (400 MHz, $CDCl_3$): 0.31 (s, 9H) 7.32-7.36 (m, 2H) 7.41-7.45 (m, 2H).

Intermediate 75.3: (4-Isopropoxy-5-methoxy-2-{[(E)-(S)-2-methyl-propane-2-sulfinylimino]-methyl}-phenyl)-acetic acid ethyl ester

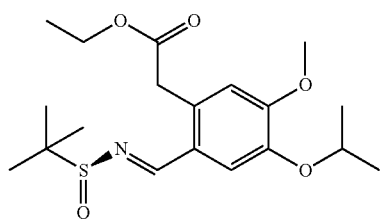 [SMILES: CCOC(=O)Cc1cc(OC)c(OC(C)C)cc1/C=N/[S@@](=O)C(C)(C)C]

To a solution of Intermediate 75.2 (9.14 g, 32.6 mmol) and (S)-(−)-2-methyl-2-propanesulfinamide (5.93 g, 48.9 mmol) in DCM (200 ml) was added $Ti(OEt)_4$ (27.3 ml, 130 mmol) at 0° C. (ice bath). The reaction mixture was heated at reflux, stirred for 5 h then cooled to RT and quenched by the careful addition of water (14.7 ml). The resulting white precipitate was filtered through a Celite pad, the filter cake was washed with DCM and the filtrate then evaporated to dryness. The resulting crude material was purified by Combi-Flash Companion™ (Isco Inc.) column chromatography ($SiO_2$; gradient elution, heptane/AcOEt 95:5→1:1) to yield the title compound (11.07 g, 28.9 mmol, 89%) as a yellow oil. TLC: $R_F$=0.40 (heptane/AcOEt 1:1); HPLC: $^At_{Ret}$=2.35 min; LC-MS: m/z 384.5 [M+H]$^+$; $^1$H NMR (400 MHz, DMSO-$d_6$): 1.17 (t, J=7.1, 3H) 1.15 (s, 9H) 1.27 (d, J=6.1, 6H) 3.83 (s, 3H) 3.94-4.07 (m, 4H) 4.58-4.66 (m, 1H) 7.04 (s, 1H) 7.50 (s, 1H) 8.49 (s, 1H).

Intermediate 75.2:
(2-Formyl-4-isopropoxy-5-methoxy-phenyl)-acetic acid ethyl ester

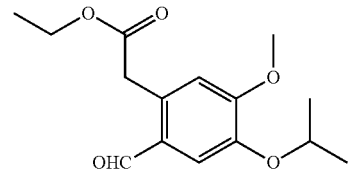 [SMILES: CCOC(=O)Cc1cc(OC)c(OC(C)C)cc1C=O]

To a solution of Intermediate 75.1 (11.94 g, 47.3 mmol) and dichloro-methoxy-methane (8.56 ml, 95 mmol) in DCM (350 ml) was slowly added $SnCl_4$ (1M solution in DCM, 95 ml, 95 mmol) over a 45 min period at 0° C. (ice bath). After the addition, the reaction mixture was further stirred at 0° C. for 45 min then poured into water and extracted with DCM (2×). The organic phase was washed with a 2M aqueous $Na_2CO_3$ solution, then dried over $Na_2SO_4$, filtered and evaporated to dryness. The resulting crude material was purified by Combi-Flash Companion™ (Isco Inc.) column chromatography ($SiO_2$; gradient elution, heptane/AcOEt 95:5→1:1) to yield the title compound (11.13 g, 39.7 mmol, 84%) as a yellow oil which crystallized on standing into an off-white solid. TLC: $R_F$=0.50 (heptane/AcOEt 1:1); HPLC: $^At_{Ret}$=1.93 min; LC-MS: m/z 281.4 [M+H]$^+$; $^1$H NMR (400 MHz, DMSO-$d_6$): 1.18 (t, J=7.1, 3H) 1.28 (d, J=6.1, 6H) 3.84 (s, 3H) 4.01 (s, 2H) 4.07 (q, J=7.1, 2H) 4.56-4.68 (m, 1H) 7.03 (s, 1H) 7.45 (s, 1H) 9.93 (s, 1H).

Intermediate 75.1:
(4-Isopropoxy-3-methoxy-phenyl)-acetic acid ethyl ester

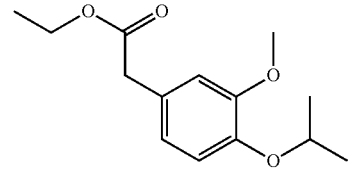 [SMILES: CCOC(=O)Cc1ccc(OC(C)C)c(OC)c1]

A mixture of ethyl (4-hydroxy-3-methoxy-phenyl)-acetic acid ethyl ester (11.22 g, 53.4 mmol) and $K_2CO_3$ (22.13 g, 160 mmol) in DMF (100 ml) was heated at 60° C. 2-Iodopropane (9.06 ml, 91 mmol) was added and the mixture was vigorously stirred at 60° C. for 5 h. The reaction mixture was cooled to RT, diluted with AcOEt and washed with water. The aqueous phase was separated and further extracted with AcOEt. The combined organic fractions were dried over $Na_2SO_4$, filtered and evaporated to dryness. The resulting crude material was purified by Combi-Flash Companion™ (Isco Inc.) column chromatography ($SiO_2$; gradient elution, heptane/AcOEt 98:2→3:1) to yield the title compound (11.94 g, 47.3 mmol, 89%) as a colorless oil. TLC: $R_F$=0.44 (heptane/AcOEt 7:3); HPLC: $^At_{Ret}$=2.14 min; LC-MS: m/z 253.4 $[M+H]^+$; $^1H$ NMR (400 MHz, $CDCl_3$): 1.28 (t, J=7.1, 3H), 1.38 (d, J=6.1, 6H), 3.56 (s, 2H), 3.87 (s, 3H), 4.17 (q, J=7.1, 2H), 4.50 (h, J=6.1, 1H), 6.77-6.89 (m, 3H).

Process to Make the Crystalline Form I of the Sulphate Salt of the Compound of Example 106:

A: Slurry Method

Solvent: isopropyl alcohol (1) About 5 mg of drug substance was first dissolved in 100 μl IPA.

(2) 364 μl 0.025N sulphuric acid was added to the solution very slowly, allowing slow precipitation during the stirring at 60° C.

(3) The suspension was stirred at room temperature overnight.

(4) The supernatant was removed by centrifugation.

(5) The solid product was dried under vacuum oven at 40° C. overnight and investigated by XRPD (X-ray powder diffraction). The process was scaled up, and scale-up samples were further characterized using XRPD. Crystalline form I was obtained.

The X-ray diffraction data were collected at room temperature using a Bruker AXS GMBH D8-Discover powder X-ray diffractometer (Cu Kα radiation) fitted with an automatic sample changer, a theta-theta goniometer, automatic beam divergence slits, a secondary monochromator and a scintillation counter. Samples were prepared for analysis by gently pressing the compound in one glass filter. The sample was rotated while being irradiated with Copper Kα1 X-rays (wavelength=1.54184 Ångstroms) with the x-ray tube operated at 40 kV/40 mA. The analyses were performed with the goniometer running in continuous mode set for a 120 second count per 0.02 degree step over a two theta range of 5 degree to 45 degree. The peaks obtained were aligned against the silicon reference standard.

Instrument Name: X-Ray Diffractometer

Model: D8 Discover

Manufacturer: Bruker AXS GMBH

Wavelength: 1.54184 A (Cu)

Generator setting: 40.00 KV, 40.00 mA

Monochromator

Detector: HI-STAR

Frame Size: 1024 pixels, 107.79 mm

Experiment Method:

2-Theta start: 5.0 degree

2-Theta end: 45.0 degree

Pixel overlap: 20%

Integration stepsize: 0.02 degree

Scan time: 120 seconds

Temperature: Room Temperature

TABLE A

XRPD data of Example 106 sulphate salt crystalline form I (A: slurry method)

| Angle 2-Theta ° | d value Angstrom | Intensity % % |
|---|---|---|
| 17.1 | 5.20 | 126 |
| 18.7 | 4.74 | 103 |
| 20.4 | 4.35 | 89.2 |
| 21.4 | 4.14 | 93.5 |
| 22.9 | 3.89 | 183 |
| 23.5 | 3.78 | 111 |
| 24.1 | 3.68 | 132 |
| 28.3 | 3.15 | 88.9 |

B: Anti-Solvent Method

Solvents: isopropyl alcohol (1) About 5 mg of drug substance was first dissolved in 91 μl 0.025N sulfuric acid IPA.

(2) Anti-solvent methyl tert-butyl ether was added to precipitate the compound during the stirring at 55-60° C.

(3) The suspension was stirred at 55-60° C. overnight.

(4) By centrifugation, the supernatant was removed.

(5) The solid product was dried in the vacuum oven at 40° C. overnight and investigated by XRPD. The process was scaled up. Scale-up samples were further characterized using XRPD. Crystalline form I was obtained.

(S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one bisulphate monohydrate was formed using this method.

TABLE B

XRPD data of Example 106 sulphate salt crystalline form I (B: Anti-solvent method)

| Angle 2-Theta ° | d value Angstrom | Intensity % % |
|---|---|---|
| 13.5 | 6.56 | 89.1 |
| 16.6 | 5.35 | 117 |
| 16.9 | 5.24 | 226 |
| 18.8 | 4.73 | 114 |
| 19.8 | 4.48 | 167 |
| 21.3 | 4.17 | 117 |
| 22.7 | 3.92 | 270 |
| 23.9 | 3.72 | 172 |
| 24.9 | 3.57 | 180 | error +/−0.2°.

It will be appreciated by the skilled crystallographer that the relative intensities of the various peaks reported in the Tables and Figures may vary due to a number of factors such as the orientation effects of the crystals in the X-ray beam, and the purity of the material being analysed. The peak positions may also shift for variations in sample weight but will remain substantially the same.

The sulphate salt formed is believed to be the bisulphate salt.

The invention also relates to the manufacture of Example 106 sulphate salt crystalline form I, as described herein.

Figure 1:
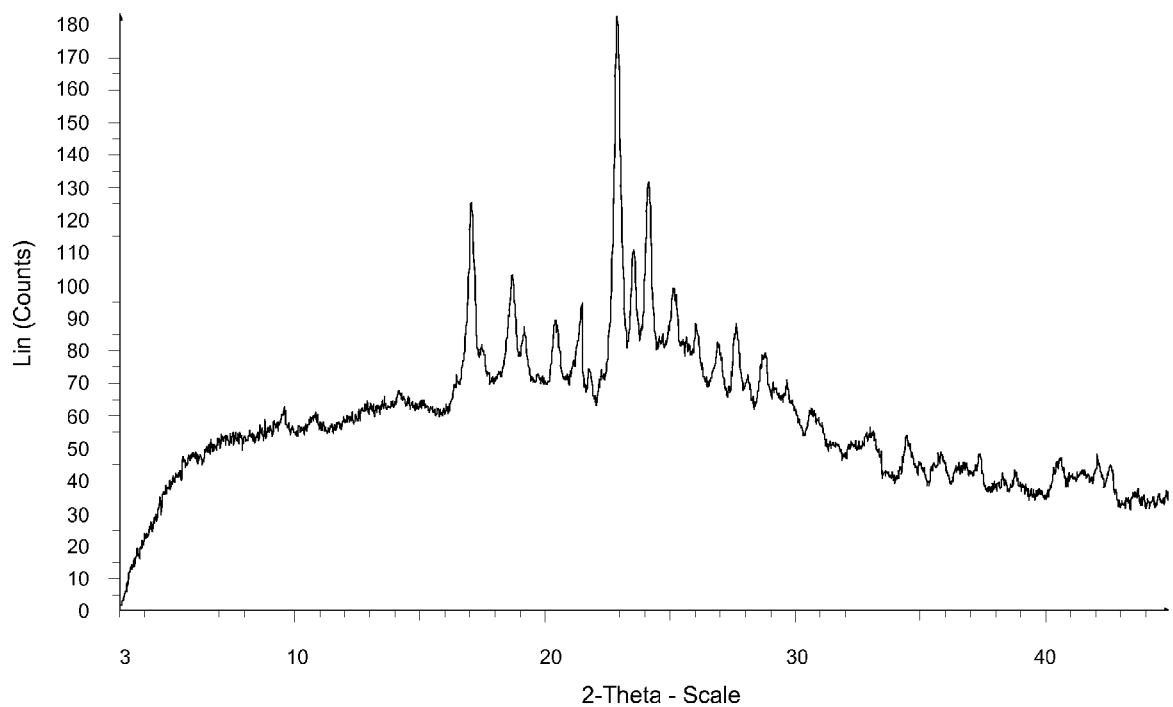
FIG. 1 discloses the X-ray powder diffraction data for Example 106 sulphate salt crystalline form I, as obtained using the slurry method.
Figure 2:
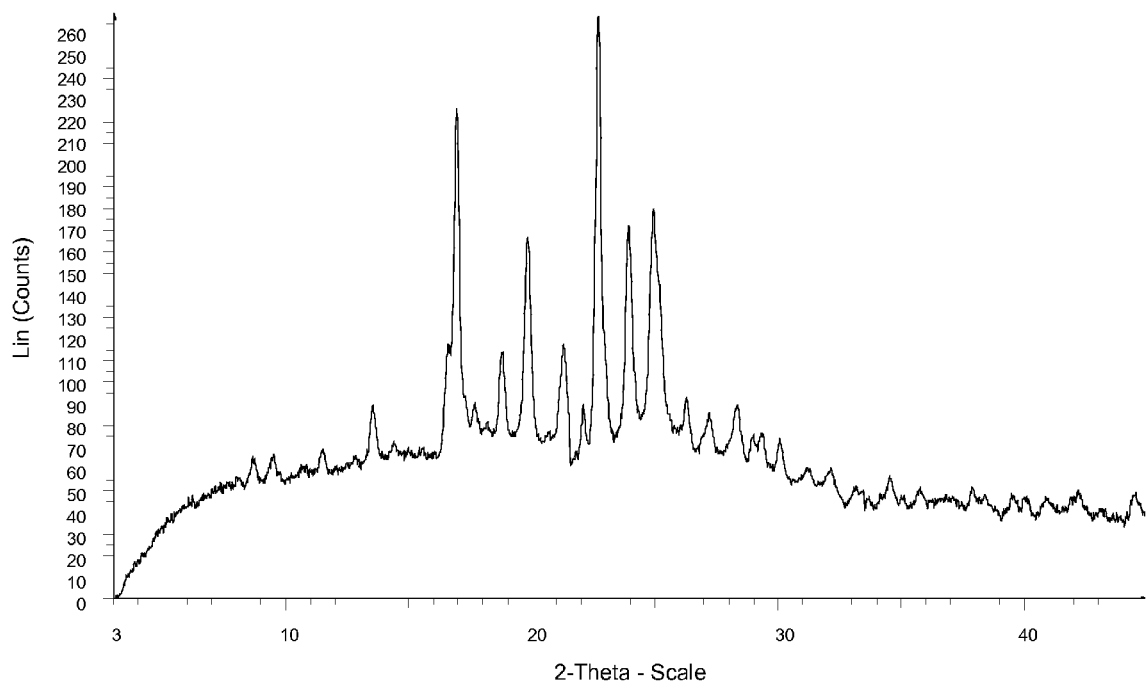
FIG. 2 discloses the X-ray powder diffraction data for Example 106 sulphate salt crystalline form I, as obtained using the anti-solvent method.

The invention claimed is:

1. A crystalline form of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one bisulphate salt.

2. A pharmaceutical composition comprising a therapeutically effective amount of the crystalline form of claim 1 and one or more pharmaceutically acceptable carriers.

3. The crystalline form of claim 1, combined with one or more therapeutic agents.

* * * * *